United States Patent

Wu

[11] Patent Number: 5,968,866
[45] Date of Patent: Oct. 19, 1999

[54] ETHYLENE TRIMERIZATION

[75] Inventor: Feng-Jung Wu, Baton Rouge, La.

[73] Assignee: BP Amoco Corporation, Chicago, Ill.

[21] Appl. No.: 09/071,643

[22] Filed: May 1, 1998

Related U.S. Application Data

[60] Division of application No. 08/519,277, Aug. 25, 1995, Pat. No. 5,815,618, which is a continuation-in-part of application No. 08/227,433, Apr. 14, 1994, Pat. No. 5,550,305, which is a continuation-in-part of application No. 08/025,524, Mar. 3, 1993, abandoned, which is a continuation-in-part of application No. 07/914,489, Jul. 14, 1992, Pat. No. 5,744,677, which is a continuation of application No. 07/777,137, Oct. 16, 1991, abandoned.

[51] Int. Cl.$^6$ .............................. B01J 31/16; B01J 31/18
[52] U.S. Cl. ..................... 502/155; 502/152; 502/154; 502/162; 502/208; 502/210
[58] Field of Search ...................................... 502/152, 154, 502/155, 162, 208, 210

[56] References Cited

U.S. PATENT DOCUMENTS

| | | | |
|---|---|---|---|
| 4,906,415 | 3/1990 | Luft et al. | 502/152 |
| 5,550,305 | 8/1996 | Wu | 585/513 |
| 5,811,618 | 9/1998 | Wu | 585/513 |

*Primary Examiner*—Elizabeth D Wood
*Attorney, Agent, or Firm*—Joseph DiSalvo; Stephen L. Hensley

[57] ABSTRACT

Ethylene is trimerized to form 1-hexene by using a catalyst comprising an aluminoxane and polydentate phosphine, arsine, and/or stibine coordination complex of a chromium salt. Catalysts, complexes, and ligands enabling production of 1-hexene in extremely high yields and purity are also described.

4 Claims, No Drawings

ETHYLENE TRIMERIZATION

REFERENCE TO RELATED APPLICATIONS

This is a divisional of U.S. application Ser. No. 08/519,277, filed Aug. 25, 1995, now U.S. Pat. No. 5,815,618; which is a CIP of Ser. No. 08/227,433 filed Apr. 14, 1994, now U.S. Pat. No. 5,550,305; which is a CIP of Ser. No. 08/025,524, filed Mar. 3, 1993, now abandoned; which is a CIP of Ser. No. 07/914,489, filed Jul. 14, 1992, now U.S. Pat. No. 5,744,677; which is a continuation of Ser. No. 07/777,137, filed Oct. 16, 1991, now abandoned.

TECHNICAL FIELD

This invention relates generally to the oligomerization of ethylene and more specifically to the preparation of 1-hexene by the trimerization of ethylene using a catalyst which includes an aluminoxane and a chromium complex containing a coordinating polydentate phosphine, stibine or arsine ligand, such as a tridentate phosphine complex of a chromium salt.

BACKGROUND

My copending U.S. application Ser. No. 07/914,489, whose teachings are incorporated herein by reference, discloses an ethylene oligomeriiation/trimerization process which uses a catalyst comprising a chromium complex which contains a coordinating polydentate ligand and an aluminoxane to produce high quality α-olefins which are enriched in 1-hexene. Suitable ligands include cyclic polyamines, and polypyrazolyl borates.

In my copending U.S. application Ser. No. 08/227,433 (which incorporates therein the disclosure of U.S. Ser. No. 08/025,524), I have shown that certain polydentate ligand complexes of chromium salts in combination with aluminoxanes can catalyze ethylene oligomerization, and especially ethylene trimerization to form 1-hexene with a very high degree of selectivity, e.g. about 96%, with formation of product containing less than 2 wt % of polyethylene. The disclosure of my copending U.S. application Ser. No. 08/227,433 is incorporated herein by reference.

Prior art ethylene trimerization processes, such as are described in U.S. Pat. Nos. 4,668,838 and 4,777,315 which use mixtures of a chromium compound, an aluminoxane and a third component selected from hydrocarbyl isonitriles, amines and ethers, are reported to produce amounts of polyethylene ranging from about 18 to 90+ percent as a coproduct. Such polyethylene not only decreases the yield of desirable product but also causes problems due to polymer build-up which would be expected to hamper the commercial use of such processes.

THE INVENTION

In sharp contrast to the results shown in U.S. Pat. Nos. 4,668,838 and 4,777,315, the present invention provides a process and catalyst systems which can readily avoid the coproduction of significant amounts of polyethylene (less than about 2.0 wt % and normally from 0 to 1.5 wt %) with most of the byproducts being useful short chain olefins, particularly 1-butene. Moreover, this invention enables the production of a hexene product of such high purity (e.g., 98 to 99% 1-hexene) that, for most commercial applications, the trouble and expense of further purification of the hexene fraction is not required. In other words, the invention makes it possible to form 1-hexene directly, while at the same time avoiding undesirable isomerization of the product to internal olefin isomers.

Moreover, it has been found possible to form high purity 1-hexene product with a catalyst productivity rate equivalent to as much as 14,000 parts by weight of product per part by weight of chromium compound used in the catalyst. The productivity of the catalysts of the above-mentioned prior art processes are limited by polyethylene formation to the range of about 500 to 1,000 g hexene/g chromium compound.

One aspect of this invention is the discovery of a new type of ligands which, when complexed with a chromium compound, provides a catalyst component exhibiting extremely high 1-hexene selectivity and yield when used in conjunction with an aluminoxane. These ligands are asymmetrical polydentate phosphines, arsines and stibines having the formula:

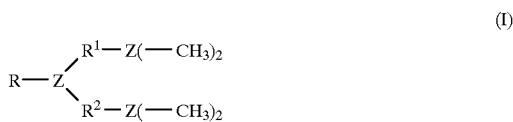

(I)

where Z, which can be the same or different, is phosphorus, arsenic or antimony, (and preferably all three of them are phosphorus atoms), R is a hydrocarbyl group, $R^1$ is a dimethylene group and $R^2$ is a linear polymethylene group having at least 3 carbon atoms, e.g., 3 to about 20 carbon atoms, preferably 3 to 6 carbon atoms, and most preferably a trimethylene group ($-CH_2CH_2CH_2-$). The makeup of R appears relatively unimportant as it can be alkyl, cycloalkyl, alkenyl, cycloalkenyl, aryl, aralkyl, etc. Typically, R will contain no more than about 12 carbon atoms, although theoretically there is no apparent reason why the hydrocarbyl group may not contain even more carbon atoms, provided the group does not sterically encumber the non-terminal Z atom to which it is attached to such an extent as to prevent the compound from forming a tridendate complex with a chromium compound. On the other hand, the makeup of the groups attached to the terminal Z atoms has a profound effect upon the excellence of the results that can be achieved by the practice of this invention. For example, experiments conducted to date with asymmetrical tridentate ligands indicate that use of an aluminoxane-chromium complex catalyst formed, for example, from a tridentate compound of the formula

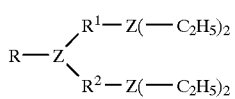

where R, $R^1$, $R^2$ and Z are as defined above, but where the terminal Z atoms are substituted by ethyl groups, may not be capable of forming an effective trimerization catalyst. In contrast, results from a catalyst derived from a similar asymmetrical tridentate compound of formula (1) above where there are methyl substituents on the terminal Z atoms, not only consistently formed trimerization product with less than 2 wt % of polyethylene, but gave much faster reaction rates, higher hexene yields, and lower internal hexene isomer formation.

The foregoing asymmetrical polydentate compounds of this invention can be formed by a two step synthesis process which comprises reacting a monohydrocarbyl phosphine, arsine or stibine with a mono(ω-alkenyl)dimethyl phosphine, arsine or stibine of the formula

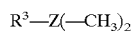

to form a disubstituted bidentate compound of the formula

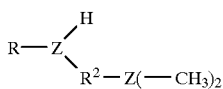

where Z, R and $R^2$ arm defined above and $R^3$ is a linear ω-alkenyl group having at least 3 carbon atoms, and then reacting this bidentate compound with dimethylvinyl phosphine to form a compound of formula (I) above. These reactions are conducted under radical-initiated addition conditions under a dry, inert atmosphere.

In accordance with another embodiment of this invention, there is provided a process for the trimerization of ethylene which process comprises reacting ethylene using a catalyst comprising an aluminoxane and a polydentate phosphine, arsine and/or stibine coordination complex of a chromium salt so as to form 1-hexene.

In a particular embodiment of this invention, this process is conducted using a polydentate phosphine, arsine and/or stibine coordination complex of a chromium salt formed from an asymmetrical polydentate phosphine, arsine and/or stibine of formula (I) above, most preferably where each Z is phosphorus.

Also provided is an ethylene trimerization catalyst composition comprising an aluminoxane and a polydentate phosphine, arsine and/or stibine coordination complex of a chromium salt.

Another particular embodiment of this invention involves conducting this process using a polydentate phosphine, arsine and/or stibine coordination complex of a chromium salt formed from an asymmetrical polydentate phosphine, arsine or stibine of formula (I) above, most preferably where Z is phosphorus.

Still another embodiment is a group of novel and eminently useful coordination complexes of a chromium salt and a polydentate phosphine, arsine and/or stibine coordination complex of a chromium salt formed from an asymmetrical polydentate phosphine, arsine or stibine of formula (I) above, most preferably where Z is phosphorus.

These and other embodiments will become still further apparent from the ensuing description and appended claims.

Aluminoxanes for use in the process of the invention can be prepared as known in the art by reacting water or water-containing materials with trialkylaluminum compounds in proportions of from about 0.5 to 1.2 equivalents of water and, preferably, 0.8 to 1.0 equivalents of water per equivalent of trialkylaluminum. For example, Manyik et al., U.S. Pat. No. 3,300,458, prepare alkylaluminoxane by passing a hydrocarbon solvent through water to form a wet hydrocarbon solvent and mixing the wet hydrocarbon solvent with an allyl aluminum/hydrocarbon solvent mixture in a conduit.

Schoenthal et al., U.S. Pat. No. 4,730,071, show the preparation of methylaluminoxane by dispersing water in toluene using an ultrasonic bath and then adding a toluene solution of trimethyl aluminum to the dispersion. Schoenthal et al., U.S. Pat. No. 4,730,072 is similar except it uses a high speed, high shear-inducing impeller to form the water dispersion.

Edward et al., U.S. Pat. No. 4,772,736, describe an aluminoxane process in which water is introduced below the surface of a solution of hydrocarbyl aluminum adjacent to a stirrer which serves to immediately disperse the water in the hydrocarbon solution.

The preparation of alkyl aluminoxanes from $R_2AlOLi$ formed by reacting $AlR_3$ and anhydrous lithium hydroxide, and $R_2AlCl$ has been reported in the literature, for example, Ueyama et al., *Inorganic Chemistry*, 12, No. 10, 2218 (1973) and Aoyazi et al., *Inorganic Chemistry*, 12, No. 11, 2702 (1973).

Sinn et al., U.S. Pat. No. 4,404,344 prepare methylaluminoxane by adding trimethyl aluminum to a slurry of $CuSO_4 \cdot 5H_2O$ in toluene. Introducing water as a metal hydrate controls its reactivity with the trimethyl aluminum. Kaminsky et al., U.S. Pat. No. 4,544,762, is similar except it uses an aluminum sulfate salt hydrate to supply the water. Likewise, Welborn et al., U.S. Pat. No. 4,665,208, describe the use of other metal salt hydrates such as $FeSO_4 \cdot 7H_2O$ as a water source in preparing aluminoxane.

Hydrocarbylaluminoxanes may exist in the form of linear or cyclic polymers with the simplest compounds being a tetraalkylaluminoxane such as tetraethylaluminoxane, $(C_2H_5)_2AlOAl(C_2H_5)_2$. Preferred aluminoxanes are prepared from trialkyl aluminum compounds such as triethyl aluminum, tri-n-butyl aluminum, triisobutyl aluminum, tri-n-hexyl aluminum, tri-octyl aluminum and the like. Of these, the more preferred are the compounds having $C_6$ or higher alkyl groups which have better solubility in the hydrocarbon solvent reaction medium. The aluminoxanes used to form the catalyst are preferably contained in organic solvents in concentrations of from about 0.3 to 30 weight percent of total solvent plus aluminoxane.

A trialkylaluminum compound can also be included in the catalyst (0.1 to 1.0 mole per mole of aluminoxane).

The chromium complexes which, upon mixing with an aluminoxane, catalyze ethylene oligomerization, and especially trimerization in accordance with the process of the invention, can be represented by the formula: $LCrX_n$, wherein L is a coordinating polydentate phosphine, arsine or stibine ligand, and X represents anions which can be the same or different and n is an integer of 2 to 4. Such complexes can be in the form of oligomers, i.e. $(LCrX_n)_y$, where y is 2 to 8. By "polydentate" is meant that the ligand contains multiple donor atoms for coordination with chromium.

Preferred polydentate ligands include the following types:
(a) $RY(R'ZR''R''')_2$
   wherein R, R" and R'" are hydrogen or $C_1$ to about $C_{20}$ hydrocarbyl and where R" and R'" can join to form a ring, especially a five-membered ring, which includes Z; R' is $C_1$ to about $C_{10}$ hydrocarbyl; and Y and Z are individually phosphorus, arsenic or antimony;
(b) $CH_3E(R'ZR''_2)_3$
   wherein E is C, Si, Ge or Sn and R', R" and Z are as defined in (a) above;
(c) $E'(R'ZR''_2)_3$
   wherein E' is nitrogen, phosphorus, arsenic or antimony and R', R" and Z are as defined in (a) above; and
(d) A-ZR-B
   wherein A is an integer of 9 to 18, B is an integer of 3 to 6, R is a $C_1$ to $C_{10}$ alkyl group such as a methyl, ethyl, propyl, butyl, pentyl, hexyl or higher allyl group or a $C_6$ to C20 aromatic group such as benzyl, and Z is phosphorous, arsenic or antimony. The abbreviations, such as 9-PR-3, 10-PR-3, 12-PR4 and the like, used for the phosphine ligands correspond to those used for crown ethers because they are their phosphorus analogues. For example, 9-PR-3 denotes a nine membered ring with 3 equally spaced phosphorus atoms. The most preferred coordinating polydentate ligands of this type are facially coordinating tridentate ligands, such as 9-PMe-3.

In the ligands of types (a), (b) and (c) each (R'ZR") moiety can be different so as to provide a mixture of donors in the same complex. The ligands of types (a), (b), (c), and (d) can be modified to attach to a polyethylene chain (molecular wt.=1000 or higher) so that the resulting catalyst is homogeneous (soluble) at elevated temperature but becomes heterogeneous (insoluble) at 25° C. This technique facilitates the recovery of the catalyst from the reaction products for reuse and has been used with other catalysts as described, for example, by D. E. Bergbreiter et al., *J. Chem. Soc., Chem. Commun.*, 337–338 (1985); *J. Org. Chem.* (1986) 51, 4752–4760; and *J. Am. Chem. Soc.* (1987), 109, 177–179.

Non-limiting examples of specific tridentate phosphine ligands include:

for type (a), EtP($C_2H_4$PEt$_2$)$_2$, whose chemical name is bis-(2-diethylphosphinoethyl)ethylphosphine;

for type (b), $CH_3C(CH_2PEt_2)_3$, whose chemical name is 1,1,1-tris(diethylphosphinomethyl)ethane;

for type (c), P($C_2H_4$PEt$_2$)$_3$, whose chemical name is tris(2-diethylphosphinoethyl)phosphine; and for type (d), 9-PMe-3, whose chemical name is 1,4,7-trirethyl-1,4,7-triphosphinocyclononane.

Other specific examples are:

$CH_3C(CH_2PPh_2)_3$ $PhP(CH_2CH_2PPh_2)_2$ $CyP(CH_2CH_2PCy_2)_2$ $PhP(CH_2CH_2PMe_2)_2$ $CyP(CH_2CH_2PMe_2)_2$ $CyP(CH_2CH_2PEt_2)_2$ n-$PrP(CH_2CH_2PEt_2)_2$ $EtP(C_3H_6PEt_2)_2$ $N(C_2H_4PEt)_3$ $PhP(o-C_6H_4PEt_2)_2$ wherein Ph=phenyl, Cy=cyclohexyl, Me=methyl, Et=ethyl and Pr=propyl.

The arsine and stibine analogs of these ligands could also be prepared, for example:

$PhAS(o-C_6H_4AsPh_2)_2$ $MeAs(o-C_6H_4AsMe_2)_2$ $MeSb(C_2H_4SbMe_2)_2$ $MeAs(C_3H_6AsMe_2)_2$

Recent experimental results indicate that at least some compounds of the formula

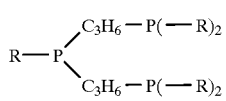

where each R is, independently, a hydrocarbyl group, such as $MeP(C_3H_6PEt_2)_2$ and $PhP(C_3H_6PMe_2)_2$, tend to form catalysts which lose activity in relatively short periods of time.

The asymmetrical polydentate phosphines, arsines and stibines of this invention (formula (I) above) are exemplified by the following:

(2-dimethylphosphinoethyl)(3-dimethylphosphinopropyl) methylphosphine;
(2-dimethylphosphinoethyl)(3-dimethylphosphinopropyl) ethylphosphine;
(2-dimethylphosphinoethyl)(3-dimethylphosphinopropyl) butylphosphine;
(2-dimethylphosphinoethyl)(3-dimethylphosphinopropyl) octylphosphine;
(2-dimethylphosphinoethyl)(3-dimethylphosphinopropyl) dodecylphosphine;
(2-dimethylphosphinoethyl)(3-dimethylphosphinopropyl) cyclohexylphosphine;
(2-dimethylphosphinoethyl)(3-dimethylphosphinopropyl) cyclohexenylphosphine;
(2-dimethylphosphinoethyl)(3-dimethylphosphinopropyl) phenylphosphine;
(2-dimethylphosphinoethyl)(3-dimethylphosphinopropyl)p-tolylphosphine;
(2-dimethylphosphinoethyl)(3-dimethylphosphinopropyl) benzylphosphine;
(2-dimethylphosphinoethyl)(3-dimethylphosphinopropyl) phenethylphosphine;
(2-dimethylphosphinoethyl)(4-dimethylphosphinobutyl) methylphosphine;
(2-dimethylphosphinoethyl)(4-dimethylphosphinobutyl) ethylphosphine;
(2-dimethylphosphinoethyl)(4-dimethylphosphinobutyl) phenylphosphine;
(2-dimethylphosphinoethyl)(4-dimethylphosphinobutyl) cyclopentylphosphine;
(2-dimethylphosphinoethyl)(5-dimethylphosphinopentyl) methylphosphine;
(2-dimethylphosphinoethyl)(5-dimethylphosphinopentyl) phenylphosphine;

and the arsine and stibine analogs corresponding to these phosphines.

By a coordinating polydentate ligand is meant a ligand that sterically encumbers the chromium atom in such a way that the rate of chain propagation is decreased so that oligomerization, especially trmerization, rather than polymerization occurs. For example, ligands which occupy three adjacent coordination sites about an octahedral chromium atom.

Examples of suitable anions, X, include, but are not limited to, halides (Cl$^-$, Br$^-$, I$^-$, F$^-$), alkoxides (OR$^-$), carboxylates ($O_2CR^-$), Oxo($O^{-2}$) and the like. These anions are initially the anion portion of the chromium compounds used to make the complex. The chromium in the compounds is initially in the oxidation state of II to VI and is preferably in the oxidation state of II, III or IV.

The known chromium complexes can be prepared according to procedures set forth in the literature. For example, L. R. Gray et al., *J. Chem. Soc. Dalton. Trans.* (1984), 47–53, A. M. Arif et al. *Inorg. Chem.*, Vol. 25, No. 8, 1986, 1080–1084, and Diel et al., *J. Am. Chem. Soc.* 1982, 104, 4700–4701. The synthesis of the novel asymmetrical ligands of this invention and chromium complexes thereof is illustrated in detail in Examples 12 through 15 hereinafter.

The chromium complex and aluminoxane are combined in proportions to provide Al/Cr molar ratios of from about 1:1 to 10,000 to 1, preferably from about 5:1 to 500 to 1. The amount of catalyst used is selected to provide the desired reaction rates at any particular reaction scale. (The presence of amounts of about 0.001 mmole or more, preferably from about 0.1 to 10 mmoles of chromium catalyst in a 300 mL reactor, are effective to catalyze the reaction.) Catalyst mixing is preferably done at low temperatures of 0 to 35° C. The presence of ethylene during catalyst mixing at these temperatures resulted in no significant difference in catalyst properties when compared with catalysts prepared in the absence of ethylene. Ethylene provided a protective effect at temperatures above 55° C.

The reaction with ethylene is carried out in an inert solvent. Any inert solvent which does not react with aluminoxane can be used. The preferred solvents are aliphatic and aromatic hydrocarbons and halogenated hydrocarbons such as, for example, toluene, xylene, ethylbenzene, cumene, mesitylene, heptane, cyclohexane, methylcyclohexane, 1-hexene, 1-octene, chlorobenzene, dichlorobenzene, and the like. The amount of solvent is not particularly critical and generally ranges from about 50 to 99 wt. percent of the initial reaction mixture.

Reaction temperatures and pressures are chosen to optimize reaction rates and selectivity. In general temperatures of from about 35 to 200° C. are used and preferably 80 to 120° C. Temperatures in the range of about 35 to about 120° C. are particularly preferred, especially when employing catalysts in which the ligand is a compound of formula (I) above. Ethylene pressures can range from atmospheric to 3000 psig preferably from about 100 to 1500 psig. Temperature and pressure affect reaction rate and purity in the following way: both higher temperature and higher ethylene pressure increase reaction rate; higher ethylene pressures give better purity by forming less internal olefins, whereas higher temperatures increase the formation of internal olefins.

The trimerization catalysts described herein may be used in a process in which trimerization and polymerization of ethylene operate simultaneously. One example of this type of process has been described in E. A. Benham, P. D. Smith, and M. P. McDaniel, *Polymer Engineering and Science*, 1988, 28, 1469.

The invention is lurrer illustrated by, but is not intended to be limited to, the following examples.

EXAMPLE 1

Preparation of Triphosphine Chromium Trichloride
Preparation of n-PrP(CH=CH$_2$)$_2$ To a 1.0 M solution of vinylMgBr (70 mmol) in THF at 0° C. was added a solution of n-PrPCl$_2$ (3.75 g, 25.9 mmol) in 35 mL THF over 1 hour. The solution was allowed to warm slowly and stirred overnight. To the resulting suspension was added degassed, saturated NH$_4$Cl solution (50 mL) slowly to kill the unreacted vinylMgBr. The organic phase was separated from the aqueous phase using a cannula. The remaining aqueous phase was washed with two 40-mL portions of Et$_2$O, which were then combined with the organic phase, dried over sodium carbonate and distilled at ambient pressure under inert atmosphere to give 2.0 g (60% yield) of n-PrP(C$_2$H$_3$)$_2$ (b.p.=143° C.).
Preparation of n-PrP(C$_2$H$_4$PEt$_2$)$_2$ A mixture of n-PrP(CH=CH$_2$)$_2$ (1.29 g, 10.0 mmol), Et$_2$PH (2.25 g, 25.0 mmol) and 2,2'-azobis(isobutyronitrile) (AIBN, 30 mg) in a closed flask under inert atmosphere was irradiated by a GE Sunlamp (275 W) one foot away for 24 hours. The resulting colorless liquid was stripped of volatiles under vacuum and vacuum distilled to give 3.1 g (97% yield) of product collected at 132–135° C./0.35 mm Hg. $^{31}$P-NMR (toluene): δ—18.5 (2P); δ—22.8 (1P).
Preparation of [n-PrP(C$_2$H$_4$PEt$_2$)$_2$]CrCl$_3$ A mixture of n-PrP(C$_2$H$_4$PEt$_2$)$_2$ (2.30 g, 7.46 mmol) and anhydrous CrCl$_3$ (0.40 g, 2.50 mmol) in a closed flask under vacuum was heated with stirring at 135° C. for 1 hour. The reaction mixture at this stage contained four compounds: excess ligand (heptane-soluble), purple LCrCl$_3$ (toluene-soluble), blue LCrCl$_3$ (CH$_2$Cl$_2$-soluble), and unreacted CrCl$_3$. Separation was achieved by solubility difference. The resulting blue cake was extracted with 20 mL of toluene, filtered, and washed with toluene until colorless. Toluene was removed from the combined purple filtrate, the residue was extracted with heptane, filtered to give a purple solid and unreacted ligand in beptane. The insoluble materials were a mixture of a blue solid and unreacted CrCl$_3$. Separation was achieved by extraction with CH$_2$Cl$_2$. Unreacted CrCl$_3$ (0.05 g) was recovered. Results: blue solid; 0.65 g, purple solid; 0.35 g. The combined yield was quantitative based on reacted CrCl$_3$. The blue and purple solids are both active in the ethylene trimerization reaction. Analysis for the blue compound, Calculated: P, 19.91; Cl, 22.79; Cr, 11.14; C, 38.60; H, 7.56. Found: P, 19.77; Cl, 23.14; Cr, 11.46; C, 38.20; H 7.65.

The following diagram shows the X-ray crystal structure of the purple product:

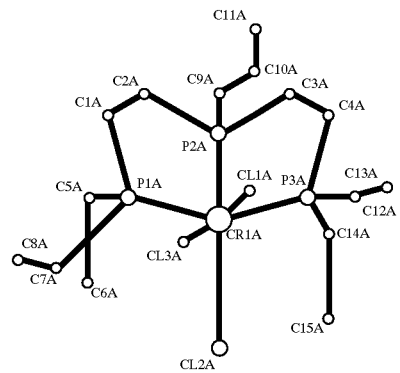

Another ligand-hromium complex, [CyP(C$_2$H$_4$PEt$_2$)$_2$]CrCl$_3$, where Cy is cyclohexyl, was prepared analogously.

EXAMPLE 2

Ethylene Tinerization Reaction

The reaction was carried out in a 300 mL Parr stainless-steel reactor to which a liquid addition bomb was connected for the purpose of adding the aluminonne solution under ethylene pressure. To the reactor containing a solution of [n-PrP(C$_2$H$_4$PEt$_2$)$_2$]CrCl$_3$ (blue compound, 45 mg, 0.096 mmol) and pentadecane (0.267 g, as internal reference for gas chromatography) in 90 mL of toluene at 25° C. under 250 psig of ethylene pressure was added a solution of n-hexylaluminoxane (5.0 mmol) in 10 mL of toluene using ethylene gas which brought the pressure to 300 psig. The chain-growth reaction was then carried out with continuous ethylene feed at 95° C./610 psig for one hour (strring rate: 800 RPM), during which time 22 g of ethylene was consumed. The reaction was terminated by pressing methanol into the reactor to deactivate the catalyst. The reactor was cooled to 10° C., vented, and a sample was withdrawn for GC analysis which showed the following results: C$_4$: 4.3%, C$_6$: 94.3%, C$_{8:\,0.2}$%, C$_{10}$: 0.9%. The polymer produced was only 0.1% and the purity of 1-hexene was 92.6% with major impurities being internal hexenes. The weights of the carbon fractions were calculated using measured response factors and minic experiments to simulate the operational loss of light olefins.

Results of this and other Examples 3–11 with varied reaction conditions are summarized in Table I. Except for Example 11, only small amounts of polyethylene were formed in the process and the butene co-product ranged from about 3 to 15 percent. Hexene production was at least 80%, Impurities in the complex can cause increased polymer formation, as per Example 11, such that if such polymer formation occurs, the purity of the complex should be checked. The process, by avoiding significant amounts of polyethylene, has the advantages that the reactions in a commercial operation would not require frequent cleaning, as would be the case with the prior art processes and also the catalyst life is extended. For example a catalyst of n-PrP($C_2H_4PEt_2$)$_2$ $CrCl_3$ retains >90% of its initial activity even after 12 hours of reaction, giving a catalyst productivity of about 8000 g hexene/g Cr catalyst compound. The catalysts according to the prior art gave catalyst productivities in the range of only 500–1,000.

(5.3 g solution, 6.0 mmol), and pentadecane (68 mg) in about 100 mL of toluene, was stirred at room temperature in a dry box for 10 minutes. No dissolution of $CrCl_3$ was observed. The mixture was poured into a Parr (300 nL) reactor, sealed, pressurized with 25 g of ethylene and heated to 96° C. The pressure was 725 psig. Because no pressure drop was observed after 17 minutes under these conditions, the temperature was brought to 125° C. As soon as the temperature reached 120° C. (800 psig) ethylene consump-

TABLE I

Catalyzed Ethylene Trimerization Reactions[1]

| Example No. | Catalyst (mmol)[2] Cr | Al | Pressure (psig) | Temperature (°C.) | Activity[3] | Distribution (wt. %) $C_4$ | $C_6$ | $C_8$ | $C_{10}$ | Purity (wt. %) 1-hexene | Polymer (wt. %) |
|---|---|---|---|---|---|---|---|---|---|---|---|
| 3 | .096 | 5.0 | 610 | 95 | 8,200 | 4.1 | 94.3 | .17 | .64 | 92.6 | 0.6 |
| 4 | .100 | 5.0 | 620 | 80 | 3,200 | 3.1 | 94.4 | .23 | .52 | 94.4 | 1.5 |
| 5 | .096 | 5.0 | 700 | 115 | 11,100 | 9.6 | 89.3 | .20 | .65 | 87.4 | 0 |
| 6 | .088 | 5.0 | 970 | 94 | 17,000 | 3.2 | 94.9 | .11 | .59 | 93.7 | 1.1 |
| 7 | .084 | 5.0 | 960 | 85 | 11,700 | 2.3 | 96.4 | 0.1 | 0.6 | 95.0 | 0.4 |
| 8 (purple [n-PrP($C_2H_4PEt_2$)$_2$]$CrCl_3$ | .069 | 5.0 | 610 | 106 | 7,800 | 8.6 | 90.3 | .23 | .62 | 90.0 | 0.1 |
| 9 (propylaluminoxane was used) | .084 | 6.0 | 610 | 94 | 5,700 | 15.0 | 83.0 | .13 | .42 | 91.9 | 1.3 |
| 10 (blue [CyP($C_2H_4PEt_2$)$_2$]$CrCl_3$ and butylaluminoxane were used) | .097 | 10.0 | 630 | 95 | 14,000 | 10.5 | 88.7 | .38 | .26 | 90.2 | 0.1 |
| 11[4] | .071 | 5.0 | 590 | 94 | 7,900 | 4.5 | 82.0 | 0.8 | 0.5 | 93.2 | 12.0 |

[1]Reactions were carried out in 100 mL toluene for one hour.
[2]Hexylaluminoxane and blue [n-PrP($C_2H_4PEt_2$)$_2$]$CrCl_3$ were used unless otherwise noted.
[3]Activity = mol ethylene/mol Cr/hr.
[4]A less pure complex was used, prepared from $CrCl_3THF_3$, which resulted in a high amount of polymer coproduct.

Comparison 1

The triphosphine ligand, n-PrP($C_2H_4PEt_2$)$_2$ was used as part of a three component $CrX_3$/aluminoxane/ligand system, where X is 2-ethylhexanoate (a mixed system as suggested in Briggs, U.S. Pat. No. 4,668,838, as opposed to a preformed chromium complex as per the process of the invention) A low yield of impure 1-hexene was formed along with a similar amount of undesirable polyethylene. The main product was butenes (72%). According to the process a mixture of n-PrP($C_2H_4PEt_2$)$_2$ (62 mg, 0.2 mmol) in toluene and Cr(2-ethylhexanoate)$_3$ in heptane (10% solution, 0.48 g solution, 0.1 mmol Cr) was allowed to react for 10 minutes with stirring in a dry box. To it was added isobutylaluminoxane (6.0 mmol) in toluene. The total amount of toluene was about 100 mL, and 115 mg of pentadecane was added as an internal reference for gas chromatography. The above mixture was transferred to a 300 mL Parr reactor, sealed, and pressured with 25 g. of ethylene (33° C./415 psig). The reaction was heated to 92–105° C. and ethylene pressure dropped from 680 psig to 390 psig over 8 minutes. After cooling, unreacted ethylene was vented at 31° C. (230 psig). The product contained 1.2 grams of polymer (12%), 1.5 grams of hexenes (15%, purity 90.9%) and 7.0 grams of butenes (72%, purity 88.6% and a trace of $C_8$ and higher materials). The results show that using a tridentate ligand as a third component, as opposed to a preformed complex with chromium, not only caused a loss of trimerization activity, but 12% polymer formation occurred. Also, a lower vinyl purity resulted. Note that this reaction used excess (2:1) ligand. Even more polymer would be expected to form if less ligand is used, based on the results obtained when using the previous 9-NMe-3 ligand.

Comparison 2

A mixture of n-PrP($C_2H_4PEt_2$)$_2$ (62 mg, 0.2 mmol), anhydrous $CrCl_3$ (23 mg, 0.15 mmol) isobutylaluminoxane tion took place. Within 5 minutes the pressure dropped from 800 to 160 psig at 120–128° C. The reactor was cooled without quenching the catalyst and unreacted ethylene was released at 30° C. The solution was light purple with about ⅔ of the $CrCl_3$ remaining unreacted. The product by GC contained 90% butenes (76.4% pure), 9% hexene (74.2% pure) and a trace of polymer. The results show that a poor yield of impure $C_6$ was produced and, although only a trace of polymer was found, the major product was butenes.

The following non-limiting examples illustrate the exceptional results achievable by producing and using the asymmetrical tridentate phosphine, arsine or stibine compounds of this invention.

EXAMPLE 12

Preparation of (2-Dimethylphosphinoethyl)(3-dimethylphosphinopropyl)phenylphosphine A. Preparation of $Me_2PCH_2CH=CH_2$ Using solvents degassed with nitrogen and conducting the operations under dry nitrogen, allyldimethylphosphine was formed by reacting dimethylchlorophosphine with allylmagnesium bromide as follows: To a clear solution of 140 mmol of allylmagnesium bromide in tetrahydrofuran (THF) was added 100 mL of diglyme, and THF was stripped from the mixture under vacuum at 25° C. until the boiling visibly slowed down. To the resulting thick, dark gray suspension in a flask wrapped in aluminum foil was added dropwise over a 50-minute period, a mixture of 108 mmol of dimethylchlorophosphine in 8 grams of diglyme. An external water bath was used to maintain the temperature of the exothermic reaction below 35° C. The reaction mixture was stirred overnight. The suspension was vacuum distilled at 25° C. under vacuum using a liquid nitrogen trap. The distillation was terminated when the boiling visibly slowed down. A near quantitative yield of product (42.33 grams) as a cloudy solution was collected and redistilled at atmospheric pressure and 16 grams of a cloudy solution was recovered between 70 and 150° C. GC showed the presence of 70.8% of allyldimethylphosphine. $^{31}$P-NMR showed only one peak at −52.5 ppm, indicating the absence of oxides and the absence of dimethylchlorophosphine.

B. Preparation of Me$_2$PCH=CH$_2$

To form dimethylvinylphosphine, the reaction of diinethylchlorophosphine with vinylmagnesium bromide was conducted in essentially the same manner as the above synthesis of allyldimethylphosphine. In particular, 100 mL of diglyme was added to 100 mL of a 1.0 molar solution of vinylmagnesium bromide in THF. The orange-brown solution was stripped under vacuum until more than 95% of the THF was removed. A mixture of 77.4 mmol of dimethylchlorophosphine in 8 grams of diglyme was added dropwise over a 25-minute period to the yellow suspension of the vinyl Grignard reagent in a flask wrapped in aluminum foil. The reaction mixture was kept at about room temperature and stirred overnight. The product solution was subjected to a low vacuum and volatiles stripped into a flask externally cooled by liquid nitrogen. The colorless product solution was found to contain 39.4% of dimethylvinylphosphine, and the product was formed in near quantitative yield. $^{31}$P-NMR showed the product to have a single peak at −48.7 ppm.

C. Preparation of PhP(M)(C$_3$H$_6$PMe$_2$)

To produce (3-dimethylphosphinopropyl) phenylphosphine a mixture of (allyl)PMe$_2$ (20.8 mmol), PHPH$_2$ (35.3 mmol), and 2,2'-azobis(isobutyronitrile) (AIBN, 0.2 g) in a 16° C. water bath with stirring was irradiated by a 275W sunlamp from ca. 20 cm away under N$_2$. After two days of irradiation, a 4:1 by weight mixture of PhP(H)(C$_3$H$_6$PMe$_2$) and PhP(C$_3$H$_6$PMe$_2$)$_2$ was obtained, along with excess PhPH$_2$. The mixture was vacuum-distilled using a 15 cm Vigreux condenser. The desired diphosphine was collected at 68–71° C./0.03 mm Hg: 12.7 mmol, 61% isolated yield. GC showed that it is contaminated by only a trace of PhPH$_2$ and ca. 0.4% of the triphosphine. $^{31}$p-NMR (toluene-d$_8$): −52.8 ppm (s, P-Me) and −53.5 ppm (s, P-Ph).

D. Preparation of PhP(C$_2$H$_4$PMe$_2$)(C$_3$H$_6$PMe$_2$)

A mixture of PhP(H)(C$_3$H$_6$PMe$_2$) (12.7 mmol), (vinyl)PMe$_2$(19 mmol), and AIBN (0.2g) in a 16° C. water bath with stirring was irradiated by a 275W sunlamp from ca. 20 cm away under N$_2$. After two days of irradiation, the resulting light yellow liquid was stripped of volatiles under vacuum at temperatures up to 90° C. The residue was flash distilled at 170° C./0.03 mm Hg to give (2-dimethylphosphinoethyl)(3-dimethylphosphinopropyl) phenylphosphine as a pale yellow liquid (11.9 mmol, 93% isolated yield). GC again showed the presence of ca. 0.4% of PhP(C$_3$H$_6$PMe$_2$)$_2$. $^{31}$P-NMR (toluene-d$_8$) revealed: −21.7 ppm (d, 23 Hz, P-Ph), −47.8 ppm (d, 23 Hz, P-C2), and −53.5 ppm (s, P-C3). Mass m/z (relative intensity): 300(4, [M$^+$]), 285 (11, M-CH$_3$), 211 (100, M-C$_2$H$_4$PMe$_2$), 197 (6, M-C$_3$H$_6$PMe$_2$).

EXAMPLE 13

Preparation of (2-Dimethylphosphinoethyl)(3-dimethylphosphinopropyl)phenylphosphine Complex of Chromium Trichloride A stirred mixture of ligand (2-dimethylphosphinoethyl)(3-dimethylphosphinopropyl)phenylphosphine (11.8 mmol) and anhydrous CrCl$_3$ (3.2 mmol) was heated at 173° C. for three hours. To the resulting purple cake after cooling was added heptane (22 g) and the suspension was filtered to separate the excess ligand. The purple solid contaminated with ca. 3–5% unreacted CrCl$_3$ was purified by dissolving in CH$_2$Cl$_2$ (17.6 g), filtering into heptane (26 g), stripping off most of the CH$_2$Cl$_2$ under vacuum, and again filtering to give the desired complex, [PhP(C$_2$H$_4$PMe$_2$)(C$_3$H$_6$PMe$_2$)] CrCl$_3$, as a purple-brown powder (2.9 mmol, 91% yield). Elemental analysis: Calculated: C: 39.32%, H: 5.96%, Cr.: 12.01%; Found: C: 39.28%, H: 5.93%, Cr.: 11.34%.

EXAMPLE 14

Preparation of (2-Diethylphosphinoethyl)(3-diethylphosphinopropyl)cyclohexylphosphine CyP(C$_2$H$_4$PEt$_2$)(C$_3$H$_6$PEt$_2$), distillable at 167–169° C. at 0.07 mm Hg, was prepared from CyPH$_2$, (vinyl)PEt$_2$, and (allyl)PEt$_2$ using procedures analogous to those of Example 12 above. Analysis by $^{31}$ P-NMR (toluene-d$_8$) revealed: −15.3 ppm (d, 19.3 Hz, P-Cy), −18.8 ppm (d, 19.3 Hz, P-C2), and −24.7 ppm (s, P-C3). Mass m/z (relative intensity): 362(2,[M$^+$]), 333 (60, M-Et), 279 (100, M-C$_6$H$_{13}$), 245 (26, M-C$_2$H$_4$PEt$_2$).

EXAMPLE 15

Preparation of (2-Diethylphosphinoethyl)(3-diethylphosphinopropyl)cyclohexylphosphine Complex of Chromium Trichloride The desired complex was prepared in 78% yield by reacting CyP(C$_2$H$_4$PEt$_2$)(C$_3$H$_6$PEt$_2$) prepared as in Example 14 with CrCl$_3$ at 162° C. for three hours. Elemental analysis revealed: Calculated: C: 43.27%, H: 7.78%, Cr: 11.42%; Found: C: 43.82%, H: 7.93%, Cr.: 9.98%.

EXAMPLES 16–23

Ethylene Trimerization Reaction

Using procedures analogous to those of Example 2 above, additional catalysts were formed from the chromium trichloride complexes of Examples 13 and 15 above—both of which were based on use of unsymmetrical tridentate phosphine ligands—and a butylaluminoxane. Both catalysts showed activity in producing 1-hexene. However, the catalyst formed by use of a novel ligand of this invention, namely, (2-dimethylphosphinoethyl)(3-dimethylphosphinopropyl)phenylphosphine gave excellent results as compared to the catalyst based on (2-diethylphosphinoethyl)(3-diethylphosphinopropyl) cyclohexylphosphine, a triphosphine compound which, per se, is not a triphosphine of this invention. These results are summarized in Table 2 (cf. Examples 16–20 versus Example 21). Table 2 also presents results recently obtained using other analogous catalysts.

TABLE 2

Catalyzed Ethylene Trimerization Reactions[1]

| Example No. | Catalyst (mmol)[2] Cr | Al | Pressure (psig) | Temperature (°C.) | Activity[3] | Distribution (wt. %) $C_4$ | $C_6$ | $C_8$ | $C_{10}$ | Purity (wt. %) 1-hexene | Polymer (wt. %) |
|---|---|---|---|---|---|---|---|---|---|---|---|
| 16[2] | .20 | 10.0 | 230 | 88 | 17,000 | 2.6 | 95.2 | — | 2.2 | 98.0 | None |
| 17[2] | .028 | 6.0 | 610 | 80 | 63,000 | 1.0 | 97.7 | — | 1.0 | 98.8 | 0.30 |
| 18[2] | .027 | 6.0 | 510 | 60 | 48,700 | 0.92 | 98.3 | — | 0.45 | 99.0 | 0.33 |
| 19[2] | .026 | 6.0 | 520 | 60 | 27,200 | 0.75 | 96.3 | — | 1.2 | 98.9 | 1.8 |
| 20[2] | .028 | 6.0 | 520 | 60 | —[4] | 0.64 | 97.6 | — | 0.96 | 99.0 | 0.78 |
| 21 | .20 | 12.0 | 610 | 86 | 440 | 53.4 | 43.8 | — | — | 95.2 | 2.7 |
| Ligand was $CyP(C_2H_4PEt_2)(C_3H_6PEt_2)$ | | | | | | | | | | | |
| 22 | .20 | 12.0 | 580 | 87 | 20,000[5] | 20.0 | 74.6 | — | — | 93.5 | 5.3 |
| Ligand was $MeP(C_3H_6PEt_2)_2$ | | | | | | | | | | | |
| 23 | .10 | 6.0 | 600 | 85 | 40,000[6] | 2.6 | 95.0 | — | 0.08 | 98.7 | 1.7 |
| Ligand was $PhP(C_3H_6PMe_2)_2$ | | | | | | | | | | | |

[1]Reaction solvent was toluene except Ex. 19 which used heptane; the aluminoxanes were either n-butyl or isobutylaluminoxane.
[2]Catalyst was based on a ligand of this invention, viz., $PhP(C_2H_4PMe_2)(C_3H_6PMe_2)$; see Example 12D.
[3]Activity = mol ethylene/mol Cr/hr.
[4]Activity was 60,000 to 34,000 for 1 hr & 50 min; 28,000 to 25,000 for 2 hr & 48 min; & 23,000 to 21,000 for 3 hr & 36 min.
[5]Reaction lasted for less than 3 minutes at which point the catalyst lost its activity.
[6]Reaction lasted for 15 minutes at which point the catalyst lost its activity.

In Example 17 the activity of the catalyst went from 160,000 to 30,000 in a 48-minute period during which time the productivity of the catalyst was 3,100 grams of olefin per gram of ligand-chromium complex. In Example 18 the activity of the catalyst went from 70,000 to 40,000 in a 45-minute period. The activity of the catalyst of Example 19 went from 37,000 to 26,000 during the first hour and remained at 26,000 over the next two hours. In this three-hour period the productivity of the catalyst was 5,500 grams of olefin per gram of ligand-chromium complex. The catalyst of Example 20 had a productivity over an 8-hour period of 14,000 grams of olefin per gram of ligand-chromium complex. It can be seen therefore that the ligand of formula (I) above formed an exceptionally effective catalyst.

Examples 24–32 further illustrate and define various embodiments of the catalyst compositions of this invention.

EXAMPLE 24

This example shows an ethylene trimerization catalyst composition comprising an aluminoxane and a polydentate phosphine, arsenic and/or stibine coordination complex of a chromium salt, wherein the mole ratio of aluminum to chromium in the catalyst is in the range of from about 1:1 to about 10,000:1; wherein said complex has the formula $LCrX_n$, where L is a coordinating polydentate phosphine, arsine and/or stibine ligand, X represents anions which can be the same or different, and n is an integer of 2 to 4; and wherein said ligand has the formula

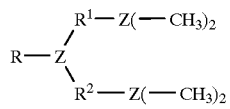

where Z, which can be the same or different, is phosphorus, arsenic or antimony, R is a hydrocarbyl group, $R^1$ is a dimethylene group and $R^2$ is a linear polymethylene group having at least 3 carbon atoms.

EXAMPLE 25

This example shows a composition according to Example 24 wherein Z is phosphorus.

EXAMPLE 26

A composition according to Example 24 wherein $R^2$ is a linear trimethylene group.

EXAMPLE 27

This example shows a composition according to Example 26 wherein Z is phosphorus.

EXAMPLE 28

This example shows a composition according to Example 27 wherein X is a halide anion and n is 3.

EXAMPLE 29

A composition according to Example 24 wherein the mole ratio of aluminum to chromium in the catalyst is in the range of from about 5:1 to about 500:1.

EXAMPLE 30

This example shows a composition according to Example 29 wherein Z is phosphorus and $R^2$ is a linear trimethylene group.

EXAMPLE 31

This example shows a composition according to Example 29 wherein said ligand is (2-dimethylphosphinoethyl)(3-dimethylphosphinopropyl)phenylphosphine.

EXAMPLE 32

This example shows a composition according to Example 29 wherein said chromium salt is a chromium trihalide and said ligand is a (2-dimethylphosphinoethyl)(3-dimethylphosphinopropyl)hydrocarbylphosphine.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

What is claimed is:

1. A polydentate phosphine, arsenic and/or stibine coordination complex of a chromium salt having the formula $LCrX_n$, where L is a coordinating polydentate phosphine, arsine and/or stibine ligand, X represents anions which can be the same or different, and n is an integer of 2 to 4; and wherein said ligand has the formula

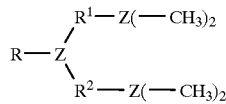

where Z can be the same or different and is phosphorus, arsenic or antimony, R is a hydrocarbyl group, $R^1$ is a dimethylene group and $R^2$ is a linear polymethylene group having at least 3 carbon atoms.

2. A complex according to claim 1 wherein Z is phosphorus and $R^2$ is a linear trimethylene group.

3. A complex according to claim 1 wherein said chromium salt is a chromium trihalide and said ligand is a (2-dimethylphosphinoethyl)(3-dimethylphosphinopropyl)hydrocarbylphosphine.

4. An ethylene trimerization catalyst composition comprising an alminoxane and a polydentate phosphine, arsenic and/or stibine coordination complex of a chromium salt, wherein the mole ratio of aluminum to chromium in the catalyst is in the range of from about 1:1 to about 10,000:1; wherein said complex has the formula $LCrX_n$, where L is a coordinating polydentate phosphine, arsine and/or stibine ligand, X represents anions which can be the same or different, and n is an integer of 2 to 4; and wherein said ligand has the formula

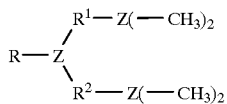

where Z can be the same or different and is phosphorus, arsenic or antimony, R is a hydrocarbyl, group, $R^1$ is a dimethylene group and $R^2$ is a linear polymethylene group having at least 3 carbon atoms.

* * * * *